United States Patent
Raymond

(10) Patent No.: US 7,515,279 B2
(45) Date of Patent: *Apr. 7, 2009

(54) LINE PROFILE ASYMMETRY MEASUREMENT

(75) Inventor: Christopher Raymond, Bend, OR (US)

(73) Assignee: Nanometrics Incorporated, Milpitas, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 10/571,418

(22) PCT Filed: Sep. 13, 2004

(86) PCT No.: PCT/US2004/030115

§ 371 (c)(1),
(2), (4) Date: Dec. 28, 2006

(87) PCT Pub. No.: WO2005/028992

PCT Pub. Date: Mar. 31, 2005

(65) Prior Publication Data

US 2007/0201043 A1     Aug. 30, 2007

Related U.S. Application Data

(63) Continuation-in-part of application No. 10/086,339, filed on Feb. 28, 2002.

(60) Provisional application No. 60/502,444, filed on Sep. 12, 2003, provisional application No. 60/273,039, filed on Mar. 2, 2001.

(51) Int. Cl.
  G01B 11/02     (2006.01)
  G01N 21/88     (2006.01)

(52) U.S. Cl. .................... 356/601; 356/636; 356/237.5

(58) Field of Classification Search .............. 356/601, 356/625, 636, 237.1–237.5
See application file for complete search history.

(56) References Cited

U.S. PATENT DOCUMENTS 4,408,884 A     10/1983     Kleinknecht et al.

(Continued)

FOREIGN PATENT DOCUMENTS

JP     03-255907 A2     11/1991

(Continued)

OTHER PUBLICATIONS

Baum, C.C. et al. (Mar. 1999). "Scatterometry for post-etch polysilicon gate metrology," Part of the SPIE Conference on Metrology, Inspection, and Process Control for Microlithography XIII, Santa Clara, California. *Proc. SPIE* 3677:148-158.

(Continued)

*Primary Examiner*—Hoa Q Pham
(74) *Attorney, Agent, or Firm*—Silicon Valley Patent Group LLP

(57) ABSTRACT

This disclosure provides methods for measuring asymmetry of features, such as lines of a diffraction grating. On implementation provides a method of measuring asymmetries in microelectronic devices by directing light at an array of microelectronic features of a microelectronic device. The light illuminates a portion of the array that encompasses the entire length and width of a plurality of the microelectronic features. Light scattered back from the array is detected. One or more characteristics of the back-scattered light may be examined by examining data from complementary angles of reflection. This can be particularly useful for arrays of small periodic structures for which standard modeling techniques would be impractically complex or take inordinate time.

33 Claims, 16 Drawing Sheets

U.S. PATENT DOCUMENTS

| | | | |
|---|---|---|---|
| 4,710,642 A | 12/1987 | McNeil | |
| 4,933,567 A | 6/1990 | Silva et al. | |
| 4,978,862 A | 12/1990 | Silva et al. | |
| 5,114,233 A | 5/1992 | Clark et al. | |
| 5,144,150 A | 9/1992 | Yoshizumi et al. | |
| 5,241,369 A | 8/1993 | McNeil et al. | |
| 5,313,542 A | 5/1994 | Castonguay | |
| 5,475,617 A | 12/1995 | Castonguay | |
| 5,637,873 A | 6/1997 | Davis et al. | |
| 5,640,246 A | 6/1997 | Castonguay | |
| 5,682,466 A | 10/1997 | Maeda et al. | |
| 5,703,692 A | 12/1997 | McNeil et al. | |
| 5,739,909 A | 4/1998 | Blayo et al. | |
| 5,864,394 A | 1/1999 | Jordan, III et al. | |
| 5,867,276 A | 2/1999 | McNeil et al. | |
| 5,889,593 A | 3/1999 | Bareket | |
| 5,905,573 A | 5/1999 | Stallard et al. | |
| 5,912,741 A | 6/1999 | Carter et al. | |
| 5,963,329 A | 10/1999 | Conrad et al. | |
| 5,982,489 A | 11/1999 | Shiraishi | |
| 6,075,594 A | 6/2000 | Thomas et al. | |
| 6,212,010 B1 | 4/2001 | Iizuka et al. | |
| 6,292,259 B1 | 9/2001 | Fossey et al. | |
| 6,292,265 B1 | 9/2001 | Finarov et al. | |
| 6,538,731 B2 | 3/2003 | Niu et al. | |
| 6,650,422 B2 | 11/2003 | Singh et al. | |
| 6,778,273 B2 | 8/2004 | Norton et al. | |
| 6,819,426 B2 | 11/2004 | Sezginer et al. | |
| 6,856,408 B2 | 2/2005 | Raymond | |
| 7,042,569 B2 | 5/2006 | Sezginer et al. | |
| 2002/0035455 A1 | 3/2002 | Niu et al. | |
| 2002/0038196 A1 | 3/2002 | Johnson et al. | |
| 2002/0046008 A1 | 4/2002 | Krukar et al. | |
| 2002/0112966 A1 | 8/2002 | Martyak et al. | |
| 2002/0131040 A1 | 9/2002 | Niu et al. | |
| 2002/0131055 A1 | 9/2002 | Niu et al. | |
| 2002/0135781 A1 | 9/2002 | Singh et al. | |
| 2002/0135783 A1 | 9/2002 | Opsal et al. | |
| 2002/0135875 A1 | 9/2002 | Niu et al. | |
| 2002/0149782 A1 | 10/2002 | Raymond | |
| 2002/0158193 A1 | 10/2002 | Sezginer et al. | |
| 2002/0165636 A1 | 11/2002 | Hasan | |
| 2002/0182760 A1 | 12/2002 | Wack et al. | |
| 2003/0002043 A1 | 1/2003 | Abdulhalim et al. | |
| 2003/0042579 A1 | 3/2003 | Schulz | |
| 2003/0043372 A1 | 3/2003 | Schulz | |
| 2003/0044702 A1 | 3/2003 | Schulz | |
| 2003/0143761 A1 | 7/2003 | Fukuda | |
| 2006/0132807 A1* | 6/2006 | Abdulhalim et al. | 356/625 |
| 2006/0262326 A1* | 11/2006 | Abdulhalim et al. | 356/625 |

FOREIGN PATENT DOCUMENTS

| | | | |
|---|---|---|---|
| JP | 03-255907 B2 | 11/1991 | |
| JP | 06-317412 A2 | 11/1994 | |
| JP | 2001-074636 A2 | 3/2001 | |
| WO | WO-00/00817 A1 | 1/2000 | |
| WO | WO 02/50501 | 6/2002 | |
| WO | WO-02/065545 A2 | 8/2002 | |
| WO | WO-02/065545 A3 | 8/2002 | |
| WO | WO-02/069390 A2 | 9/2002 | |
| WO | WO-02/069390 A3 | 9/2002 | |
| WO | WO-02/070985 A1 | 9/2002 | |
| WO | WO-02/077570 A1 | 10/2002 | |
| WO | WO-2005/028992 A2 | 3/2005 | |
| WO | WO-2005/028992 A3 | 3/2005 | |

OTHER PUBLICATIONS

Bischoff, J. et al. (1998). "Optical scatterometry of quarter micron patterns using neural regression," *Proc SPIE* 3332:526-537.

Bischoff, J. et al. (Aug. 2001). "Light diffraction based overlay measurement," Metrology, Inspection and Process Control for Microlithography XV, *Proc. SPIE* 4344:222-233.

Bushman, S. et al. (1997). "Scatterometry Measurements for Process Monitoring of Polysilicon Gate Etch," Process, Equipment, and Materials Control in Integrated Circuit Manufacturing III, *Proc. SPIE* 3213:79-90.

Davidson, M.P. et al. (Mar. 1999). "An inverse scattering approach to SEM line width measurements," Part of the SPIE Conference on Metrology, Inspection, and Process Control for Microlithography XIII, Santa Clara, California. *Proc. SPIE* 3677:640-649.

Ding, P. et al. (Oct. 23, 2000). "Light Scattering Study of Roughness and Dishing on Post-CMP Wafers," *Abstract from Fourth International Symposium on Chemical Mechanical Polishing (CMP)*, 198th Meeting: Phoenix, Arizona. 18 pages.

International Search Report mailed on Jul. 20, 2005 for PCT Application No. PCT/US2004/030115 filed on Sep. 13, 2004, two pages.

International Search Report mailed on Jun. 27, 2002 for PCT Application No. PCT/US02/06403 filed on Feb. 28, 2002, one page.

Kallioniemi, I.J. et al. (May 1999). "Optical Scatterometry with neural network model for nondestructive measurement of submicron features," Part of the EUROPTO Conference on In-line Characterization Techniques for Performance and Yield Enhancement in Microelectronic Manufacturing, Edinburgh, Scotland. *Proc SPIE* 3743:33-40.

Krukar, R.H. et al. (1992). "Novel diffraction techniques for metrology of etched silicon gratings," Optical Society of America, Washington, D.C., *OSA Annual Meeting Technical Digest* 23:204.

Krukar, R.H. et al. (1992). "Wafer examination and critical dimension estimation using scattered light," Machine Vision Applications in Character Recognition and Industrial Inspection, D'Amato et al. eds., *Proc. SPIE* 1661:323-332.

Moharam, M.G. et al. (May 1995). "Formulation for stable and efficient implementation of the rigorous coupled-wave analysis of binary gratings," *J. Opt. Soc. Amer. A.* 12(5):1068-1076.

NMRC Scientific Reports. (1999). "Laser Scatterometry," located at <http://www.nmrc.ie/reports/1999/scientific/sciphoto.html> last updated Aug. 18, 2006. *Photonics*, pp. 1-11.

Raymond, C.J. et al. (1997). "Resist and etched line profile characterization using scatterometry," *Integrated Circuit Metrology, Inspection, and Process Control XI, Proc. SPIE* 3050:476-486.

Raymond, C.J. et al. (2000). "Scatterometry for the measurement of metal features," Metrology, Inspection, and Process Control for Microlithography XIV, *Proc. SPIE* 3998:135-146.

Sohail, S. et al. (Nov./Dec. 1994). "Diffractive techniques for lithographic process monitoring and control", *J. Vac. Sci. Technol. B* 12(6):3600-3606.

Supplementary European Search Report mailed on Feb. 15, 2007 for EP Application No. 02 70 9756.7, three pages.

CN First Office Action mailed on Feb. 25, 2005 for Application No. 02805890.9 filed on Feb. 28, 2002, English translation included, twelve pages.

CN Second Office Action mailed on Nov. 4, 2005 for Application No. 02805890.9 filed on Feb. 28, 2002, English translation included, six pages.

CN First Office Action mailed on Jul. 6, 2007 for Application No. 200480033229.X filed on Sep. 13, 2004, thirteen pages.

Preliminary Amendment mailed on Jun. 3, 2003 for U.S. Appl. No. 10/086,339, filed on Feb. 28, 2002, ten pages.

Office Action mailed on Dec. 22, 2003 for U.S. Appl. No. 10/086,339, filed on Feb. 28, 2002, twelve pages.

Response to Office Action mailed on May 27, 2004 for U.S. Appl. No. 10/086,339, filed on Feb. 28, 2002, thirteen pages.

Notice of Allowance mailed on Jun. 21, 2004 for U.S. Appl. No. 10/086,339, filed on Feb. 28, 2002, four pages.

European Search Report mailed on Jun. 26, 2008 for European Patent Application No. 04784089.7 filed on Sep. 13, 2004 by Accent Optical Technologies, Inc., 5 pgs.

Murnane, Michael R. et al., "Subwavelength photoresist grating metrology using scatterometry", Proceedings of SPIE, vol. 2532 (1995) pp. 253-262.

Raymond, Christopher J. et al., "Asymmetric line profile measurement using angular scatterometry", Proceedings of SPIE, vol. 4344 (2001) pp. 436-446.

Raymond, Christopher J. et al., "Scatterometry for shallow trench isolation (STI) process metrology", Proceedings of SPIE, vol. 4344 (2001) pp. 716-725.

* cited by examiner

LINE PROFILE ASYMMETRY MEASUREMENT

CROSS-REFERENCE TO RELATED APPLICATIONS

The present application is a U.S. National Phase application of PCT/US2004/030115, filed Sep. 13, 2004. Further, this application is a continuation-in-part of U.S. patent application Ser. No. 10/086,339, filed Feb. 28, 2002, which claims the benefit of U.S. Provisional Patent Application No. 60/273,039, filed Mar. 2, 2001. This application also claims the benefit of U.S. Provisional Patent Application No. 60/502,444, filed Sep 12, 2003. The entirety of each of these applications is incorporated herein by reference.

BACKGROUND

1. Field of the Invention (Technical Field)

The present invention relates to optical inspection of microelectronic devices, in particular measurement of line profile asymmetry using scatterometry.

2. Background Art

Note that the following discussion refers to a number of publications by author(s) and year of publication, and that due to recent publication dates certain publications are not to be considered as prior art vis-à-vis the present invention. Discussion of such publications herein is given for more a complete understanding and is not to be construed as an admission that such publications are prior art for patentability determination purposes.

The fabrication of a microelectronic device is a complicated procedure that uses a variety of equipment for the different process steps involved. First, the lithography process transfers the image being made into a light sensitive material known as photoresist. This image in photoresist, in turn, acts as a mask for the next patterning process known as etching. Etching is the process by which the resist image is transferred into a suitable material such as poly-silicon. Then the etched material is over-filled with some insulating materials, planarized if necessary, and the whole process begins again.

Throughout the entire process the devices being made should be symmetric in nature from step to step, i.e., a correctly manufactured transistor gate will have equal left and right sidewalls as well as other features such as, but not limited to, equal left and right corner rounding. If errors occur during the processing, this desired symmetry may be compromised, and as a result the device integrity or functionality may also be compromised. If the asymmetry is quite severe the device may not function at all.

The present invention relates to performing symmetry/asymmetry measurements via scatterometry. Scatterometry is an optical inspection technique well suited for the measurement of symmetry or asymmetry on microelectronic devices. By analyzing the light scattered from an array of microelectronic features, measurements of the line profile can be made. In particular, a scatterometer that measures at complementary angles, i.e., +45 degrees from a position perpendicular to the surface and −45 degrees, is ideally suited for symmetry/asymmetry measurements because the reflectance properties of the line profile can vary at these angles, although complementary angles are not necessarily needed to detect asymmetry. To enhance the sensitivity of this effect the array of features should be placed in a particular orientation, known throughout the specification and claims as a general conical configuration, namely one in which the wave vector of the illuminating beam does not remain parallel to the array's plane of symmetry.

Prior art techniques typically employ "classic" scattering. These are measurements geared towards the measurement of surface roughness, defects, pitting, etc. However, the present invention is based on the physics of diffraction, with the measurements in the invention always occurring with respect to periodic features (such as line/space gratings).

Prior work in scatterometry used the technique for the measurement of line profiles in resist and etched materials. C. J. Raymond, et al., "Resist and etched line profile characterization using scatterometry," *Integrated Circuit Metrology, Inspection and Process Control XI, Proc. SPIE* 3050 (1997). Embodiments of the present invention provide techniques for the measurement of asymmetric line profiles (e.g., unequal sidewall angles).

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION

Overview

Figure 1:
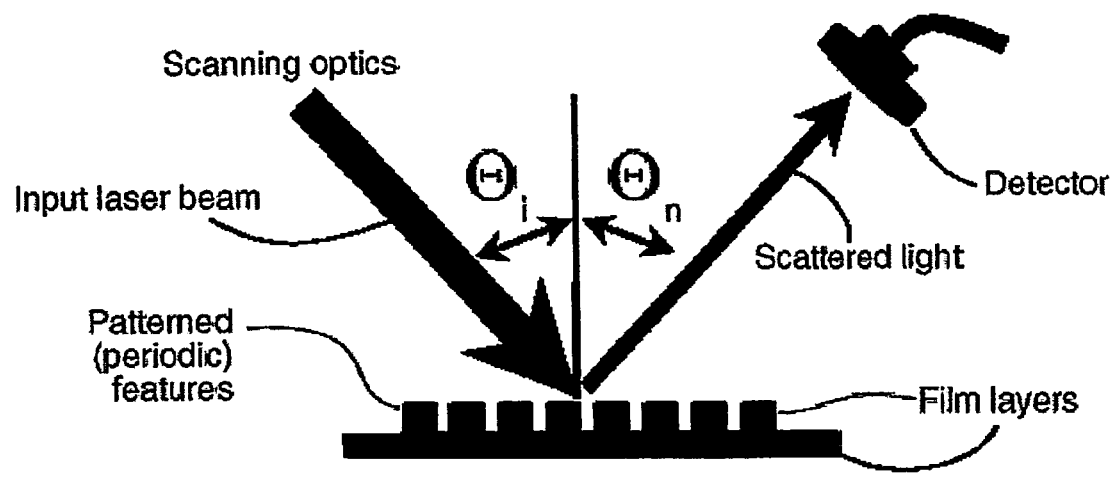
FIG. 1 is a block diagram of the angular scatterometer employed in an embodiment of the present invention.

Aspects of the present invention provide methods and apparatus for measuring symmetry/asymmetry of an array of microelectronic features. One embodiment of the invention provides a method of measuring three-dimensional structure asymmetries in microelectronic devices. In accordance with this method, light is directed at an array of microelectronic features of a microelectronic device. The light illuminates a portion of the array that encompasses the entire length and width of a plurality of the microelectronic features. Light scattered back from the array is detected at a condition selected from the group consisting of one or more angles of reflection, one or more wavelengths, or a combination thereof. The method also includes examining one or more characteristics of the back-scattered light by performing an operation comprising examining data from complementary angles of reflection A method of measuring line profile asymmetries in microelectronic devices in accordance with another embodiment of the invention involves directing light at an array of microelectronic features of a microelectronic device at an angle of incidence to the array. Light scattered back from the array is detected at an angle complementary to the angle of incidence. One or more characteristics of the detected light is compared to an asymmetric model that includes a single feature profile that, in transverse cross-section, has an upper surface, a base and a midline. The midline extends between the upper surface and the base and perpendicularly to the base and the cross section is asymmetrical about the midline.

Methods of Scatterometry

By analyzing electromagnetic radiation scattered from an array of microelectronic features, measurements of the line profile can be made. In some preferred embodiments, a scatterometer measures at complementary angles, e.g., +45 degrees and −45 degrees from a position perpendicular to the surface; this has proven to be particularly well suited for symmetry/asymmetry measurements because the reflectance properties of the line profile can vary at these angles. To enhance the sensitivity of this effect, the array of features is preferably placed in a particular orientation, known as a general conical configuration. Scatterometers in accordance with other embodiments measure at non-complementary angles, though.

Scatterometry measurements can be performed at any complementary angles—+/−45 degrees is one example, but suitable pairs of complementary angles range from nearly 0° to nearly +/−90°, e.g., about +/−0.00001° to about +/−80°; one useful embodiment performs scatterometry measurements at complementary angles of about +/−0.00001° to about +/−47°. (One cannot measure reflectance at an angle complementary to a 0° angle of incidence, so 0.00001° is arbitrarily selected here as a nominal angle; any other nominal angle may suffice.) The scatterometry measurements may by performed at several angles or a series of angles. Furthermore, measurements at each angle may include radiation of a single wavelength (such as a laser), or may include radiation composed of several wavelengths or broad wavelength radiation (such as a white light source). The intensity of the radiation alone might be measured, or the intensity and phase can be measured in tandem, similar to an ellipsometry measurement.

The optimum electromagnetic radiation source will depend on the nature and size of the grating. To improve clarity, though, the following discussion generally refers to the electromagnetic radiation as light. Regardless of the light source used or the manner in which it is measured, assuming the array is oriented in the general conical configuration, comparing data from complementary angles can immediately show if an asymmetry is present. Without any additional need for analysis, if the light measurements are the same then the profile is symmetric. Conversely, if the light measurements differ then the profile is asymmetric. In general, as more complementary angles are used, the better the measurement sensitivity. This makes angular scatterometers (those that scan through angle) better suited than spectral scatterometers (those that scan through wavelength) for these measurements of profile asymmetry. In some embodiments, the scatterometer can scan through a range of angles and a range of wavelengths.

Applications of the complementary angle scatterometry method of the invention include, but are not limited to:
- alignment of a wafer stage with an optical system, such as that on a lithography tool (stepper or scanner) or in a lithography process;
- alignment of wafer with an optical system, such as that on a lithography tool (stepper or scanner) or in a lithography process
- determination of the lens aberrations present in a lithography tool or process;
- general diagnostic of the imaging performance of a lithography tool or process;
- measurement of the temperature uniformity of a bake process/station;
- measurement of the thickness uniformity of resist spin coaters or spin processing;
- measurement of the uniformity of a developer process/station;
- characterization of an etch tool or process;
- characterization of a planarization tool or process;
- characterization of a metallization tool or process; and
- control of any of the aforementioned processes.

In the most general sense, one goal of semiconductor processing is to produce a device (e.g., a transistor gate) that is inherently symmetric. Indeed, it is rare that a device is produced that is intentionally non-symmetric or asymmetric. To this end the lithography patterning process is geared towards symmetry, particularly with regards to footing at the bottom of a line and equivalent sidewalls. Likewise, etch processing also strives to produce symmetric features, in this case mostly with respect to line sidewalls. For control of either of these processing steps, then, measurement techniques must be able to detect asymmetry, and preferably be able to measure any asymmetry present (such as unequal left and right sidewalls).

Scatterometry is an optical metrology based on the analysis of light scattered from a periodic array of features. In a strict physical sense, this light "scattered" from a periodic sample is actually due to diffraction, but in a general sense it is termed scatter here for purposes of discussion. When a series of periodic features (known as a diffraction grating) is illuminated with a light source, the reflectance properties of the scattered/diffracted light depend on the structure and composition of the features themselves. Therefore, by analyzing the scatter "signature" one can determine the shape and dimensions of the diffraction grating.

Diffraction can actually give rise to a number of different "orders," or light beams, scattered from the features. In modern semiconductor production geometries, the period of the features is small and therefore typically only one diffraction order exists. This order is known as the "specular" or "zeroth" order and is the light beam most frequently used in scatterometry technology. One of the more common ways of analyzing light scatter using the specular order is to vary the incidence angle of the illuminating light source (which is usually a laser). As FIG. 1 illustrates, as the incident angle $\Theta_i$ is varied and a detector moves in tandem at angle $\Theta_n$ to measure the diffracted power of the specular order, a scatter "signature" is measured. It is this scatter signature—known as an angular signature—that contains information about the diffracting structure, such as the thickness of the grating and the width of a grating line. This angular signature, when measured properly, can also contain information about any asymmetry present in the grating lines as well. By measuring through complementary angles (both positive and negative with respect to normal), a signature can be obtained that is asymmetric if the line is asymmetric. Conversely, if the line profile is in fact symmetric, the measured signature will also be symmetric. Complementary angles are not needed, however, if a suitable theoretical diffraction model is available for comparison purposes, and the "inverse" problem (see below) can be performed.

The scatterometry method is often described in two parts, typically known as the "forward" and "inverse" problems. In the simplest sense the forward problem is the measurement of a scatter signature, and the inverse problem is the analysis of the signature in order to provide meaningful data. Many types of scatterometers have been investigated over the years, e.g., C. J. Raymond, et al., "Metrology of subwavelength photoresist gratings using optical scatterometry, *Journal of Vacuum Science and Technology B* 13(4), pp. 1484-1495 (1995); S. Coulombe, et al., Ellipsometric scatterometry for sub 0.1 μm measurements, *Integrated Circuit Metrology, Inspection and Process Control XII, Proc. SPIE* 3332 (1999); Z. R. Hatab, et al., Sixteen-megabit dynamic random access memory trench depth characterization using two-dimensional diffraction analysis, *Journal of Vacuum Science and Technology B* 13(2), pp. 174-182 (1995); and X. Ni, et al., Specular spectroscopic scatterometry in DUV lithography, *Proc SPIE* 3677, pp. 159-168 (1999). The most widely studied, though, have been the angular or "2-$\Theta$" (because of the two theta variables shown in FIG. 1) variety where, as mentioned earlier, the incident angle is varied in order to obtain a scatter signature. It is this type of scatterometer that is preferred, but not necessary, for the measurement of line profile asymmetry. It should be noted that the scanning optical system in FIG. 1 allows this angular scatterometer to measure both positive and negative angles from normal incidence (0 degrees) up to approximately +/−47 degrees.

Several different approaches have also been explored for the solution of the inverse problem. C. J. Raymond, et al. (1995), supra; R. H. Krukar, Ph.D. Dissertation, University of New Mexico (1993); J. Bischoff, et al., *Proc SPIE* 3332, pp. 526-537 (1998); and I. J. Kallioniemi, et al., *Proc SPIE* 3743, pp. 33-40 (1999). Because the optical response of a diffraction grating can be rigorously simulated from Maxwell's equations, the most common methods are model-based analyses. These techniques rely on comparing the measured scatter signature to signatures generated from a theoretical model. Both differential and integral models have been explored. Because these diffraction models are computationally intensive, standard regression techniques generally cannot currently be utilized without introducing errors due to the performance of the regression, but if the errors are small or tolerable, a regression approach could be used. Generally, however, the model is used a priori to generate a series of signatures that correspond to discrete iterations of various grating parameters, such as its thickness and the width of the grating lines. The set of signatures that results when all parameters are iterated over some range of values is known as a signature library. When the scatter signature is measured, it is compared against the library to find the closest match. Standard Euclidean distance measures, such as minimizing the mean square error (MSE) or root mean square error (RMSE), are used for identifying the closest match. The parameters of the modeled signature that agrees most closely with the measured signature are taken to be the parameters of this measured signature. Scatterometers in some embodiments preferably include analysis software that is based on error minimization.

In previous research scatterometry has been used for the measurement of critical dimensions (CDs) and profile characterization of photoresist samples, C. J. Raymond, et al. (1995), supra; and C. Baum, et al., "Resist line width and profile measurement using scatterometry," *SEMATECH AEC-APC Conference,* Vail, Colo., (September 1999), as well as etched materials such as poly-silicon and metals, S. Bushman, et al., "Scatterometry Measurements for Process Monitoring of Polysilicon Gate Etch," *Process, Equipment, and Materials Control in Integrated Circuit Manufacturing III, Proc. SPIE* 3213 (1997); C. Baum, et al., "Scatterometry for post-etch polysilicon gate metrology," *Integrated Circuit Metrology, Inspection and Process Control XIII, Proc. SPIE* 3677, pp. 148-158 (1999); and C. Raymond, et al., "Scatterometry for the measurement of metal features," *Integrated Circuit Metrology, Inspection and Process Control XIV, Proc. SPIE* 3998, pp. 135-146 (2000). Because the technology is rapid, non-destructive and has demonstrated excellent precision, it is an attractive alternative to other metrologies used in mainstream semiconductor manufacturing. In particular, scatterometry is quite amenable to measurements of asymmetry because, as will be demonstrated, angular scatter "signatures" can quickly show (without performing the inverse problem) if any asymmetry is present on the grating lines.

Figure 2:
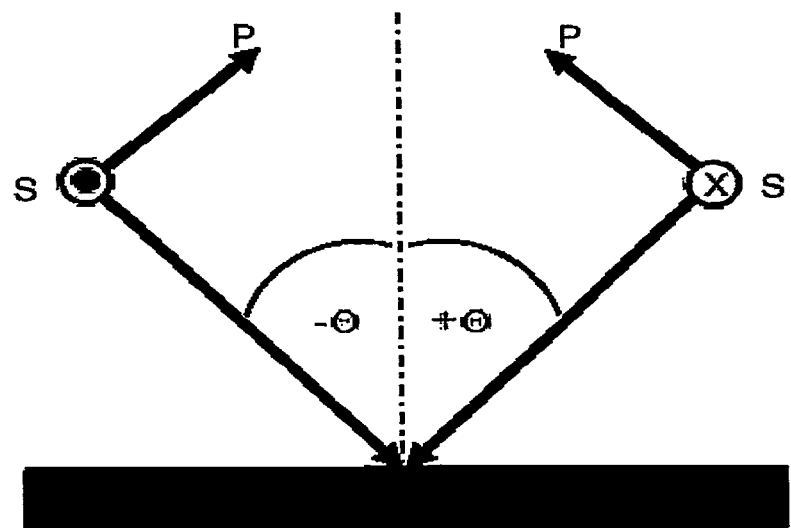
FIG. 2 illustrates the geometry of the angular scatterometry measurement employed by an embodiment of the invention.

When considering whether or not to expect symmetry in the measured diffraction efficiency of the specular (zero order) scatter signature, it is convenient to decompose both the input and output fields into S and P components relative to the input boundary of the grating problem (in this case the xy-plane). FIG. 2 illustrates the geometry of these components relative to the angular scan direction (scans from both the positive and negative angular regions are shown). Note that the plane of incidence shown in this figure is the page itself, and no reference has yet been made with respect to the orientation of the grating relative to this plane of incidence. From the figure we can see that there is a phase difference in the S polarization component when the beam moves from one half of the angular region to the other. This phase difference is one reason why an asymmetric angular signature can be produced from an asymmetric line profile.

Figure 3:
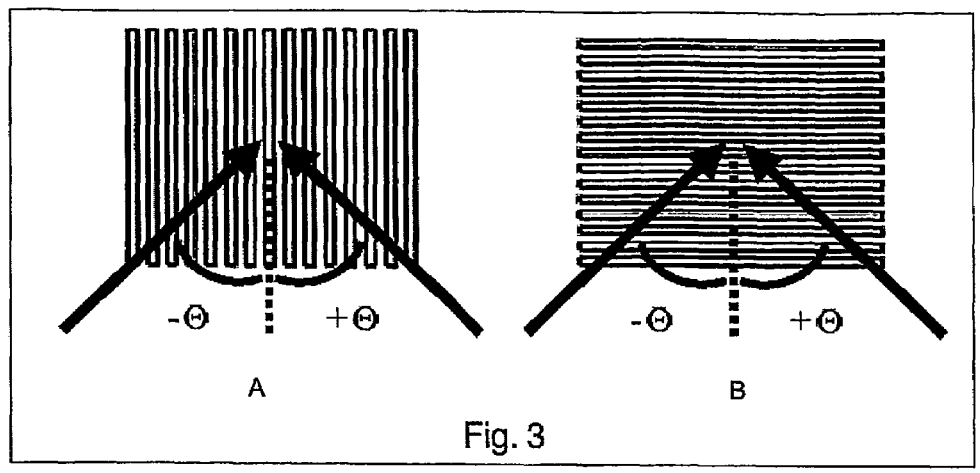
FIGS. 3(a) and (b) illustrate, respectively, so-called conventional and conical scatterometry measurement orientations.

Grating orientation relative to the plane of incidence is another consideration in the measurement of sample asymmetry. FIGS. 3A and 3B depict two orientations, known as the conical and conventional configurations, respectively. From first principles it can be shown that a scan parallel to the grating vector (the so-called "normal" or "conventional" configuration shown in FIG. 3A) is the only case that never couples the S and P modes of the total electromagnetic field (see, for example, equation (48) of M. Moharam, et al., "Formulation for stable and efficient implementation of the rigorous coupled-wave analysis of binary gratings," *J. Opt Soc. Amer. A,* Vol. 12, pp. 1068-1076 (May 1995)). For general conical scattering problems, if the input illumination is in a pure P-polarization state the coupled nature of the problem tells one that one may observe both S and P components in the output (total) field. Similarly, if the input illumination is in a pure S-polarization state then we may observe both S and P components in the output (total) field.

The scattering problem is linear and so the principle of superposition holds. If a mixed polarization state is used for the input wave we may decompose the input field into S and P components, solve the problems separately, and then superpose the resulting output fields in complex amplitude. The S component of the total output field is composed of contributions from both the S and P portions of the input field due to the fully coupled nature of the problem. A similar statement is true of the P component of the total output field. The superposition takes place in complex amplitude and thus field components in the S-polarization state coming from S and P portions of the input field exhibit interference effects. This means that relative phase differences between the S and P components of the total input field can translate into amplitude differences in the S and P components of the total output field. With this in mind one expects asymmetry in output diffraction efficiencies for any case where coupling is present. It should also be noted that in a strict conical scan (the wave vector of the illuminating beam remains parallel to the structure's plane of symmetry), a symmetric structure produces no coupling. Hence, for this case one expects symmetry in the measured diffraction efficiencies. Only in the case of an asymmetric structure or a general conical scan (the wave vector of the illuminating beam does not remain parallel to the structure's plane of symmetry) with both S and P components present in the input beam does one expect asymmetry in the measured S and P diffraction efficiencies.

Figure 4:
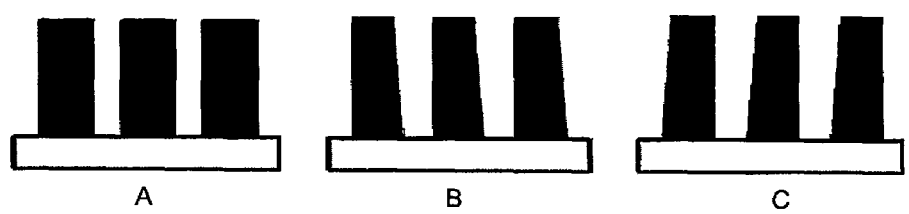
FIGS. 4(a)-(c) illustrate, respectively, a symmetric and two asymmetric resist profiles.
Figure 5:
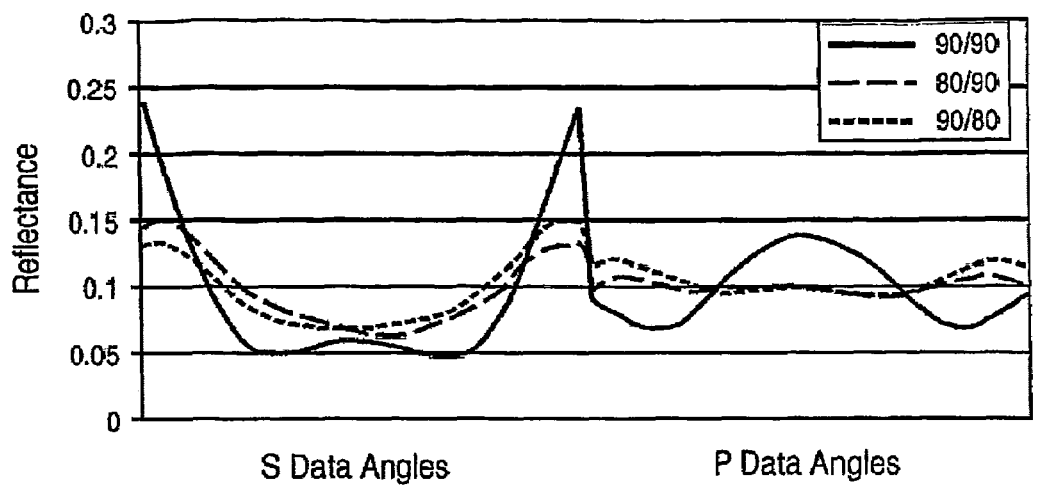
FIG. 5 is a graph of angular signature data corresponding to the profiles of FIGS. 4(a)-(c).

To introduce this concept of asymmetric grating lines giving rise to asymmetric measured scatter signatures, consider the simple photoresist line profiles shown in FIGS. 4(*a*)-(*c*). FIG. 4(*a*) depicts a perfectly symmetric profile with both wall angles equal to 90 degrees. In FIG. 4(*b*), the right wall angle has been changed to 80 degrees, while in FIG. 4(*c*) the opposite case is illustrated (left at 80 degrees, right back to 90 degrees). FIG. 5 shows the angular scatter signatures—measured through complementary angles—associated with each of these profiles. As can be seen in the figure, the symmetric profile yields a symmetric scatter signature for both polarizations. However, the asymmetric profiles show a significant amount of asymmetry in both polarizations. In fact, the signatures appear to be skewed, or "tipped," as a result of the profile asymmetry. Furthermore, a comparison of the signature data for the 80/90 and 90/80 degree cases shows an interesting result—the reversal of the sidewall angles yields a reversal of the signature. Physically this reversal would be the same as rotating the wafer through 180 degrees and thereby transposing the positive and negative regions of the scan, so this result is self-consistent. These figures also illustrate the advantage of angular scatterometry for determining the presence of asymmetry since one could establish that the profiles were non-symmetric with mere visual investigation of the signatures.

Asymmetric Model Comparison

In other embodiments, asymmetry could be determined by performing the solution to the inverse problem, e.g., performing a model comparison, either by way of a regression or through the use of a library comparison. This may be advantageous if only "half-sided" (positive or negative) angles were present, for example, or if the system was a spectral scatterometer operating at a fixed angle.

Figure 19:
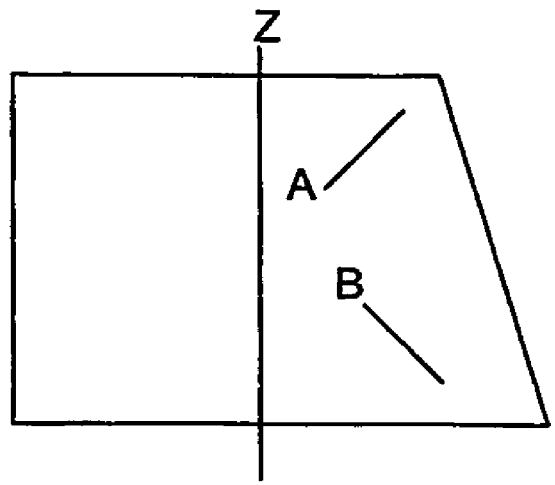
FIG. 19 illustrates an asymmetric single line model of an embodiment of the invention, wherein two angles are right, angle A is obtuse and angle B is acute, such that the cross section provides three different angles.
Figure 20:
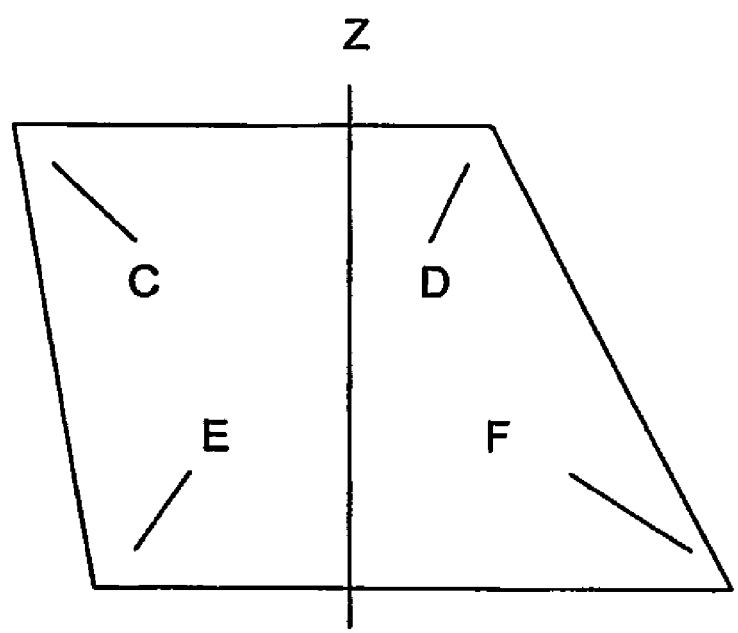
FIG. 20 illustrates an asymmetric single line model of an embodiment of the invention, wherein all four internal angles differ, with angles C and F being acute and E and D being obtuse.
Figure 21:
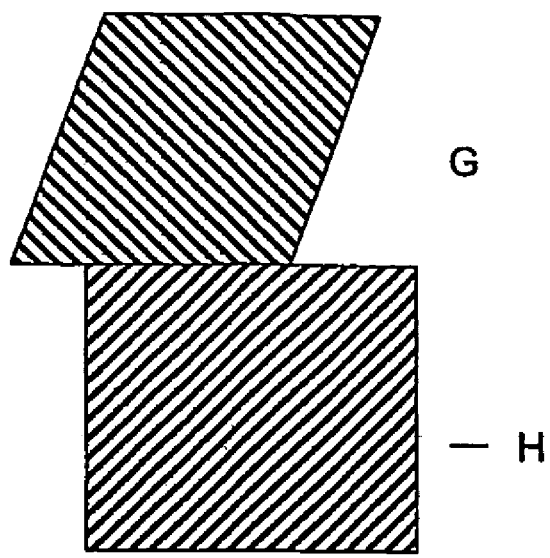
FIG. 21 illustrates a line overlay asymmetric model of an embodiment of the invention, wherein line H is rectangular and line G is both offset with respect to sidewall alignment and further is a non-rectangular parallelogram.
Figure 22:
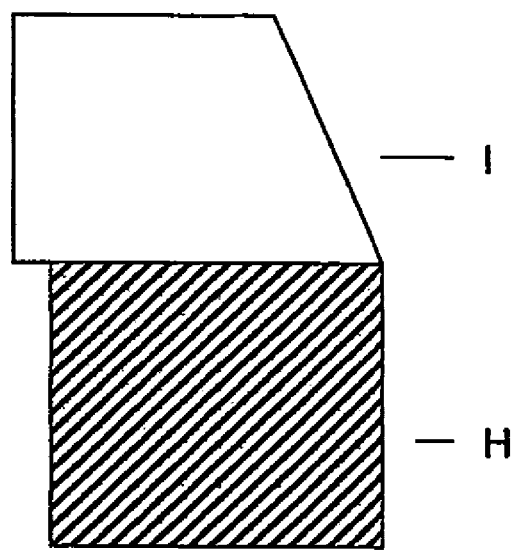
FIG. 22 illustrates a line overlay asymmetric model of an embodiment of the invention, wherein line H is rectangular and line I is offset with respect to sidewall alignment on one side, but not on the other side, and further where the cross section of line I provides three different angles.

FIGS. 19 to 24 illustrate some structures in which model comparison may be useful. Each of these drawings is a transverse cross-section of a feature, which may be referred to as a feature profile. In some embodiments, the features may be lines of a diffraction grating and the transverse cross-section may be substantially perpendicular to a longitudinal axis (not shown) of the line. Some of the illustrated feature profiles, e.g., FIGS. 19 and 20, are single line profiles. Others, e.g., FIGS. 21 and 22, are overlaid or multi-layer diffraction structures that may comprise two or more features. FIG. 21, for example, may be though of as a feature profile that comprises a first single line profile G overlaid upon a second line profile H; in FIG. 21, an asymmetric single line profile I instead overlays the symmetric single line profile H.

Each of the model feature profiles of FIGS. 19-24 is asymmetric. Looking first at FIG. 19, the feature profile 100 includes a base 102, a top 104, and left and right sidewalls 106 and 108, respectively. An ideal symmetrical may have a top 104 parallel to the base 102 that meet parallel sidewalls 106 and 108 at right angles. In FIG. 19, the left sidewall 106 is vertical, but the right sidewall 108 slants. Consequently, the feature profile 100 is asymmetrical about a midline Z that extends between the top 102 and the base 104 and is perpendicular to the base. In FIG. 19, the midline Z is positioned equidistant from the left-most point of the feature (sidewall 106) and the right-most point of the feature (where sidewall 108 joins the base 102), but there is no midline perpendicular to the base 102 about which the feature profile 100 is symmetrical. The single line profile 110 of FIG. 21 also includes a base 112, a top 114 parallel to the base, and two sidewalls 116 and 118. Neither of the sidewalls 116 and 118 is vertical, but the left sidewall 116 is slanted at one angle to vertical and the right sidewall 118 is slanted at another angle to vertical. The feature profile 110 therefore is asymmetrical about midline Z.

Figure 23:
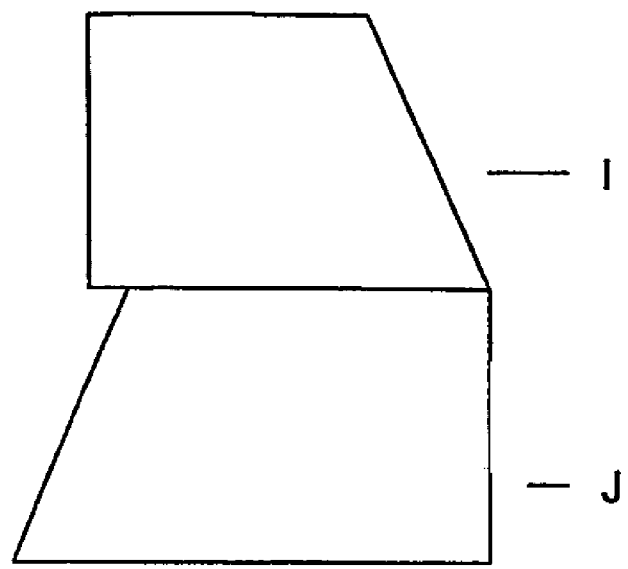
FIG. 23 illustrates a line overlay asymmetric model of an embodiment of the invention, wherein line I is offset with respect to sidewall alignment on one side with respect to line J, but not on the other side, and further where the cross section of each of line I and J provides three different angles.
Figure 24:
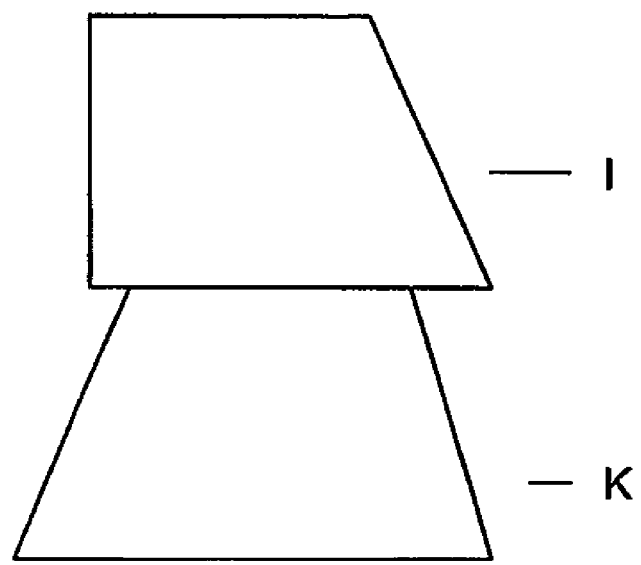
FIG. 24 illustrates a line overlay asymmetric model of an embodiment of the invention, wherein line I is offset with respect to sidewall alignment on both sides with respect to line J, where the cross section of line I provides three different internal angles and the cross section of line K provides four different internal angles.

Multi-layered features may include a feature profile in one layer that is symmetrical, such as line H in FIGS. 21 and 22, and one that is asymmetrical, such as line G in FIG. 21 and line I in FIG. 22. The lower line profile J in FIG. 23 is not perfectly rectangular, but it is symmetrical—a midline (not shown) perpendicular to the middle of the base of the line would yield two symmetrical halves. Despite the symmetry of the feature profiles of one layer of the structure in FIGS. 21-23, the overall feature profile is asymmetrical. In other embodiments, the model feature profile may have two or more single-layer feature profiles that are asymmetrical. For example, FIG. 24 illustrates a two-layered feature in which both the upper feature profile I and the lower feature profile K are asymmetrical about a vertical midline (not shown).

Many of the model feature profiles of FIGS. 19 to 24 include at least three different angles. As a result, the two angles on the left side of the profile may be right angles, but angles A and B differ from one another and neither is a right angle. Certain of the model figures, such as FIG. 20 and line K of the multi-layer diffraction structure of FIG. 24, have four different angles within a transverse cross-section of a feature. In FIG. 20, each of the included angles of the feature profile, i.e., angles C, D, E, and F, is different from the others. In some overlaid or multi-layer diffraction structures, at least one, and optionally two or more, of the overlaid features has at least three different angles within a cross-section of a line.

In one embodiment of the invention, a theoretical library of single or multi-layer diffraction structures and corresponding simulated or theoretical diffraction signals, such as diffraction signatures, is generated, with theoretical diffraction signatures based on the theoretical single or multi-layer diffraction structures compared to the measured diffraction signature. This may be done by any number of different methods. In one approach, an actual library of theoretical output signals are generated based on assigned parameters for variables. This library may be generated prior to actual measurement of a diffraction signature or may be generated in a process of matching the measured diffraction signature to a theoretical diffraction signature. Thus, as used herein, a theoretical library includes one or both of a library generated independent of the measured diffraction signature and a library generated based on a theoretical "best guess" of the geometry of the measured undercut multi-layer structure and calculation of the resulting theoretical diffraction signature, with iterative comparison to changed parameter structures to determine a best match. The library may optionally be pruned by removing signals that may be accurately represented via interpolation from other signals in the reference set. An index of the library can similarly be generated by correlating each signature with one or more indexing functions and then ordering the index based on the magnitude of the correlation. Construction or generation of libraries of this type, and methods for optimization thereof, are well known in the art.

In one approach, a rigorous, theoretical model based on Maxwell's equations is employed to calculate a predicted optical signal characteristic of the diffraction structure, such as the diffraction signature, as a function of diffraction structure parameters. In this process, a set of trial values of the diffraction structure parameters is selected and a computer-representable model of the diffraction structure, including its optical materials and geometry, is constructed based on these values. The electromagnetic interaction between the diffraction structure and illuminating radiation is numerically simulated to calculate a predicted diffraction-signature. Any of a variety of fitting optimization algorithms may be employed to adjust the diffraction structure parameter values, with the process iteratively repeated to minimize discrepancy between the measured and predicted diffraction signature, thereby obtaining the best match. U.S. Published Patent Application No. US 2002/0046008 discloses one database method for structure identification, while U.S. Published Patent Application No. US 2002/0038196 discloses another method. Similarly, U.S. Published Patent Application No. US 2002/0135783 discloses a variety of theoretical library approaches, as does U.S. Published Patent Application No. US 2002/0038196.

Generation of libraries from a model pattern is well known in the art, as disclosed in a number of references, such as U.S. Patent Application Publication Nos. 2002/0035455, 2002/0112966, 2002/0131040, 2002/0131055 and 2002/0165636, among others. Early references to these methods include R. H. Krukar, S. S. H. Naqvi, J. R. McNeil, J. E. Franke, T. M. Niemczyk, and D. R. Hush, "Novel Diffraction Techniques for Metrology of Etched Silicon Gratings," *OSA Annual Meeting Technical Digest,* 1992 (Optical Society of America, Washington, D.C., 1992), Vol. 23, p. 204; and R. H. Krukar, S. M. Gaspar, and J. R. McNeil, "Wafer Examination and Critical Dimension Estimation Using Scattered Light," *Machine Vision Applications in Character Recognition and Industrial Inspection,* Donald P. D'Amato, Wolf-Ekkehard Blanz, Byron E. Dom, Sargur N. Srihari, Editors, *Proc SPIE,* 1661, pp 323-332 (1992).

Other approaches to matching, including real-time regression analysis, may similarly be employed. These methods are known in the art, and may be employed to determine a "best fit" theoretical diffraction signal, such as a diffraction signature, based on model permutation, such as permutation in a single line or multi-layer diffracting structure. In the technique generally described as iterative regression, one or more simulated diffraction signatures are compared to a measured diffraction signature, thereby creating a difference of error signal, with another simulated diffraction signature then calculated and compared to the measured diffraction signature. This process is repeated or iterated until the error is reduced, which is to say regressed, to a specified value. One method of iterative regression is non-linear regression, which may optionally be performed in a "real-time" or "on-the-fly" mode. Different iterative regression algorithms, familiar to those skilled in the art, may be applied to interpretation of measured diffraction signatures through comparison with simulated diffraction signatures based on model structure profiles.

In addition to the parameters associated with single or multi-layer patterns as disclosed herein, other diffraction structure parameters that may be utilized in a theoretical library include any parameter that may be modeled, including factors such as the period of a grating; materials parameters of the structure, including parameters of various layers thereof; materials parameters of the substrate on which a structure is placed, such as film thickness and index of refraction of films underneath the structure; and various weighted or average values, such as CD at a specified location, values weighted by relative contributions of the structure and substrates, or the like.

In yet another embodiment, short periodic structures may be modeled and the results may be utilized, e.g., by a regression or model comparison. As used herein, the term "short periodic structures" encompasses three-dimensional structures that have lengths short enough so that the entire length and width of two or more of the structures can be encompassed in an area illuminated by the light source of the scatterometer to be used. If the area illuminated by the intended scatterometer is on the order of 40 μm wide, for example, the short periodic structures may have a longitudinal length (e.g., in a direction perpendicular to the k vector of a grating) that is less than 40 μm and a transverse spacing (e.g., the distance along the k vector of a line grating between adjacent lines of a line grating) short enough to encompass at least two of the features. Desirably, the length of the short periodic structures is less than one half of the width of the illuminated area so that at least two, and preferably three or more, of the short periodic structures may be spaced from one another yet fit longitudinally within the illuminated area. Preferably, the length of the short periodic structures is short enough to become a relevant parameter with respect to the incident illumination.

In one exemplary embodiment, each of the lines of a line grating model is defined as a series of longitudinally aligned short lines instead of a single long line. For example, each of the short lines may be about 5-20 μm long, about 0.2-1 μm wide, and about 0.5-2 μm wide. The period between parallel lines may be about 0.5-2 μm. The entire length and width of many of the short lines of this structure would be encompassed by illumination if a scatterometer's incident radiation covered a circular area having a diameter of about 40 μm.

Figure 25:
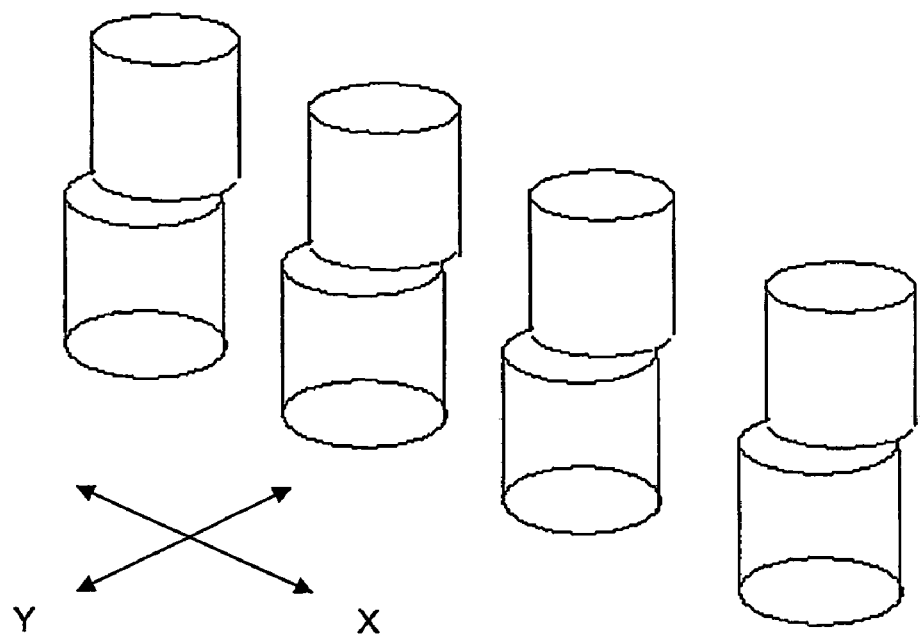
FIG. 25 is an illustration, which may be employed as a model in one embodiment of the invention, wherein a first series of three-dimensional posts are deposited on top of and skewed in the x and y orientations with respect to a second series of posts, such that the posts are off-set or contain a stair-step feature.
Figure 26:
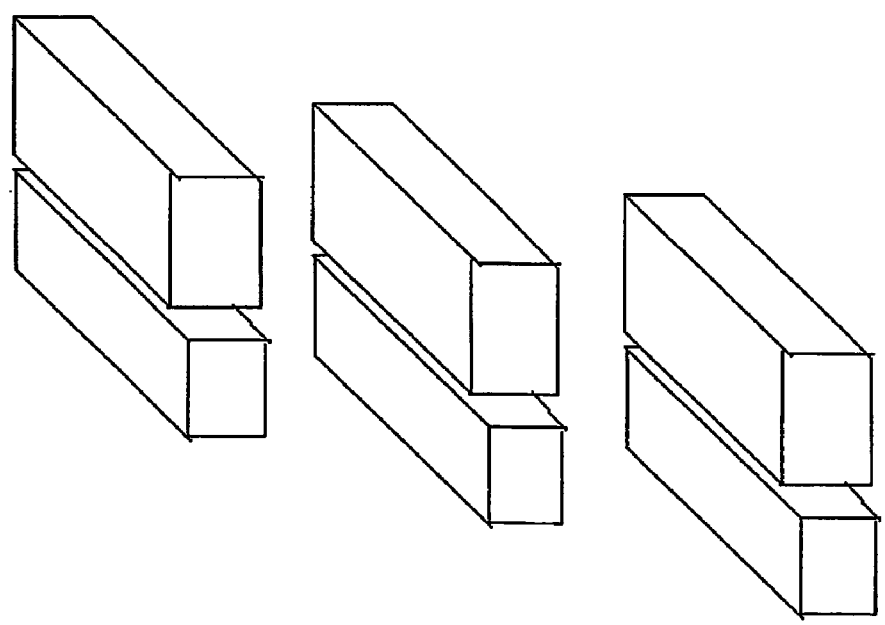
FIG. 26 is an illustration, which may be employed as a model in one embodiment of the invention, wherein a first series of three-dimensional rectilinear structures are deposited on top of and skewed in the x and y orientations with respect to a second series of rectilinear structures, such that the structures are off-set or contain a stair-step feature.
Figure 27:
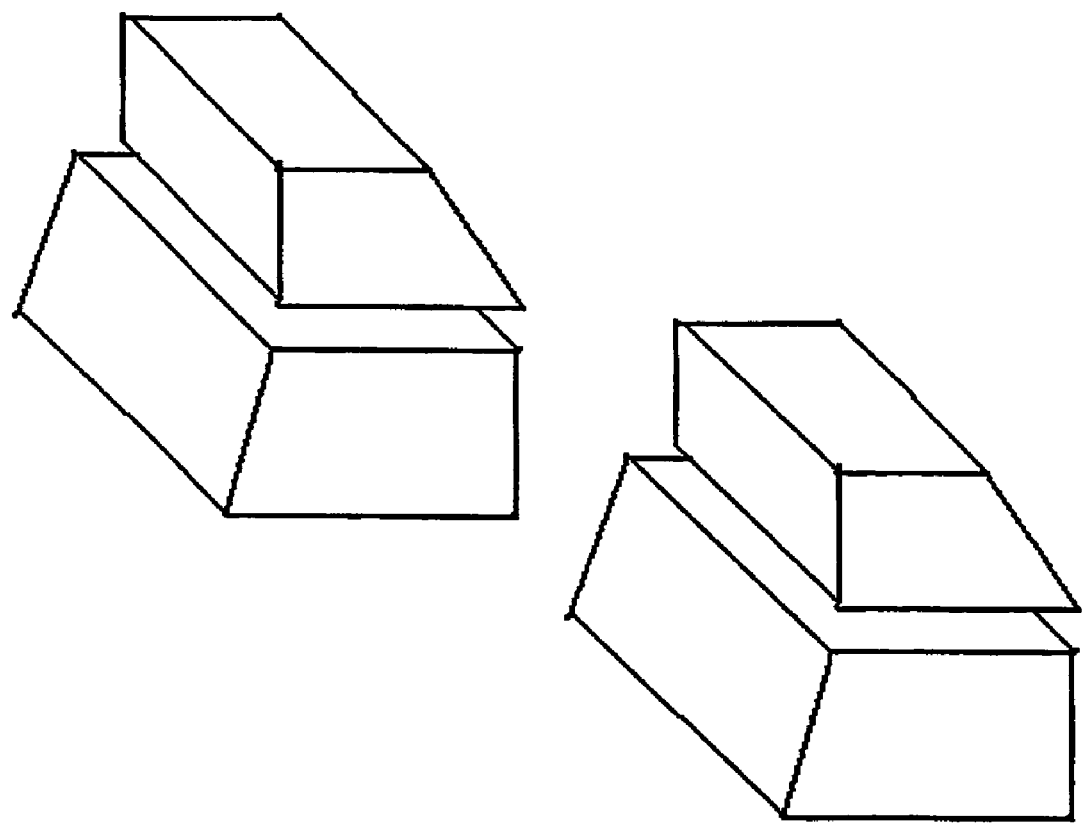
FIG. 27 is an illustration, which may be employed as a model in one embodiment of the invention, wherein a first series of three-dimensional rectilinear structures are deposited on top of and skewed in the x and y orientations with respect to a second series of rectilinear structures, and further wherein the cross-section of at least one of the rectilinear structures is not rectangular and provides at least three different internal angles.

FIGS. 25-27 schematically illustrate short periodic structures in accordance with select embodiments of the invention. In FIG. 25, each of the short periodic structures comprises an array of features, each of which includes a first post or hole that overlays another post or hole. The axis (not shown) of the first post or hole in each of these features is offset from the axis of the second post or hole, yielding a two-layer feature that contains a "stair-step" shape. In a preferred embodiment, the posts are oval in shape, preferably an elongated oval, thereby providing the greatest resolution with respect to complementary angle analysis. The array may be arranged as a series of lines of the features that is periodic in the X-direction, but need not be periodic in the Y-direction. In one useful model, the array is a regular array of posts or holes that have periodicity in both in the X-direction and Y-direction. In FIG. 26, a first series of rectilinear features are deposited on top of and skewed in the x and y orientations with respect to a second series of rectilinear features, such that the structures are offset or contain a "stair-step" feature as in FIG. 25. FIG. 27 also includes a first series of rectilinear features deposited on top of and skewed in the x and y orientations with respect to a second series of rectilinear features. Unlike FIGS. 25 and 26, the transverse cross-section of at least one of the rectilinear features is asymmetrical and provides at least three different internal angles. In the specific implementation shown in FIG. 27, both of first and second features are asymmetrical, similar to lines I and J of FIG. 23. In one useful embodiment, the dimensions of the structure in the horizontal dimension (with respect to the plane of the device) are different, preferably substantially different. In FIG. 26, for example, the short lines are substantially longer (in the X-direction of FIG. 25) than they are wide (in the Y-direction of FIG. 25). While simple circular and rectangular structures are depicted in FIGS. 25-27, methods in accordance with other embodiments of the invention may employ any three-dimensional structure, but preferably a repeating or periodic structure.

Some implementations of the invention employ a theoretical model based on the three-dimensional structure of an array of short periodic structures. While computing a three-dimensional model is complex because of the large number of variables in such a structure, it is possible to generate a model, and use this model for comparison and analysis purposes with data acquired on the actual three-dimensional structure using scatterometry techniques discussed above. It is also possible and contemplated that such as the three-dimensional model will utilize various algorithms and methodologies designed to simplify computation of the model.

In yet another embodiment, asymmetry in an array of three-dimensional short periodic features by measuring complementary angles (both positive and negative with respect to normal), and preferably by measuring through a range of complementary angles $\ominus$ (again both positive and negative with respect to normal). A signature can be obtained that is asymmetric if the three-dimensional structure is asymmetric. Conversely, if the three-dimensional structure is in fact symmetric, the measured signature will also be symmetric.

Figure 28:
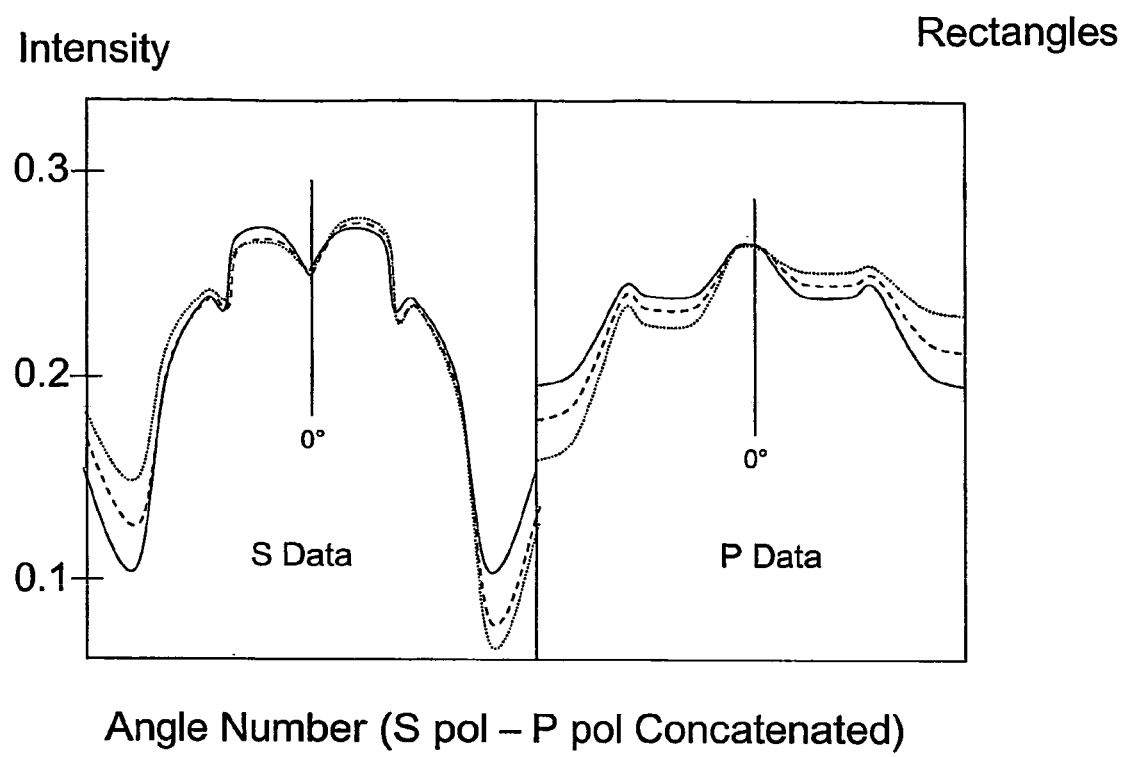
FIG. 28 is a graph of angular scatterometry signatures (mirrored over complementary ranges) of a first series of rectangular three-dimensional rectilinear structure deposited on top of a second series of rectangular structures structure as in FIG. 25, wherein the solid line depicts no offset with respect to the first and second series, the dashed line depicts a 25 nm offset, and the dotted line depicts a 50 nm offset.
Figure 29:
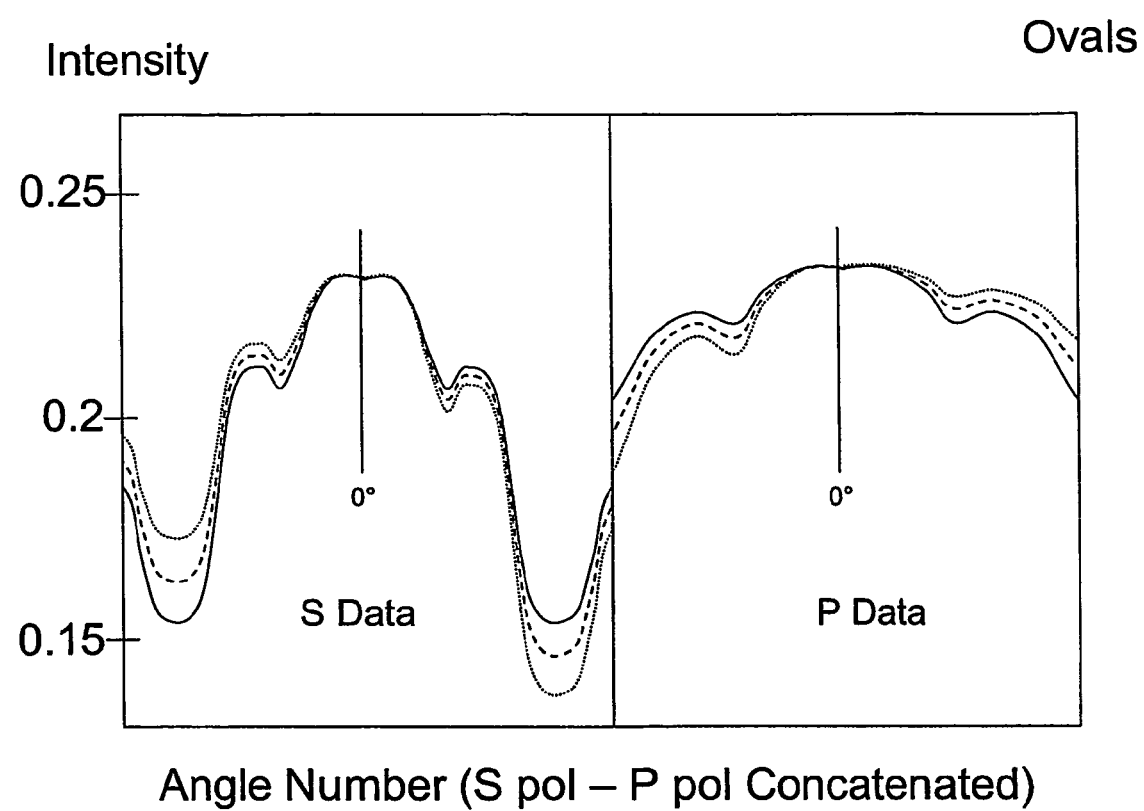
FIG. 29 is a graph of angular scatterometry signatures (mirrored over complementary ranges) of an oval post-on-post structure (as in FIG. 26), with a first series of three-dimensional oval-shaped posts deposited on top of a second series of like-shaped posts, wherein the solid line depicts no offset with respect to the first and second series, the dashed line depicts a 25 nm offset, and the dotted line depicts a 50 nm offset.

The utility of the invention in determining asymmetry in three-dimensional structures by comparison of complementary angles, such as over a range, is graphically depicted in FIGS. 28 and 29. FIG. 28 is a graph of angular scatterometry signatures (mirrored over complementary ranges) of a first series of rectangular three-dimensional rectilinear structure deposited on top of a second series of rectangular structures structure as in FIG. 26. In FIG. 28, the solid line depicts no offset with respect to the overlaid single features, the dashed line depicts a 25 nm offset of these single features, and the dotted line depicts a 50 nm offset. The S-polarized measurements and the P-polarized measurements are symmetric about the 0° angle where there is no offset (the solid line). With 25 nm offset (the dashed line) each profile (such as the S Data profile or the P Data profile) is "skewed" about 0° such that each of the S Data and P Data plots are asymmetric. As the asymmetry of the three-dimensional structure increases, the asymmetry in the resulting plots correspondingly increases, such that the asymmetry is greater at a 50 nm offset (the dotted line) than it is at a 25 nm offset (the solid line).

FIG. 29 is a graph of angular scatterometry signatures (mirrored over complementary ranges) of an oval "post-on-post" three-dimensional structure similar to FIG. 25, wherein a first series of oval-shaped posts is deposited on top of a second series of like-shaped posts. The solid line in FIG. 29 depicts no offset with respect to the first and second series, the dashed line depicts a 25 nm offset, and the dotted line depicts a 50 nm offset. As in FIG. 28, the degree of asymmetry within the S Data and in the P Data correlates to the degree of asymmetry in the three-dimensional structure.

Taking scatterometry measurements of short periodic structures at complementary angles in accordance with embodiments of the invention, therefore, requires comparatively very little computational power. Modeling of three-dimensional structures is intensely computational, and rigorous models of all by the simplest structures cannot readily be obtained in reasonable periods of time with current computational devices and programs. However, embodiments of the invention that measure at complementary angles may identify asymmetry by examining the symmetry of the collected data, which is simpler and easier from a computational perspective.

Scatterometry is thus particularly applicable to three-dimensional structures-on-structures, with scatterometry measurements of the $0^{th}$, or specular, diffraction order sensitive to alignment shifts in the successive three-dimensional structure layers. This shift in the three-dimensional structure layer (also referred to as an offset) results in an asymmetric line profile, and that can be measured using a scatterometer in the proper measurement orientation. As is seen, the signatures change when offsets are introduced, which is a positive sign for general measurement sensitivity. The measurement orientation can be, in one embodiment, empirically determined based on the specific nature of the most critical three-dimensional measurement (e.g., whether the most critical measurement is in the x, y or z direction). Thus in addition to varying the angle $\Theta$ over a range (and taking measurement of the corresponding complementary angle in each instance), it is also possible to vary the angle $\Phi$ (the rotational angle), and determine the optimal angle $\Phi$ for the three-dimensional measurement to be made.

The examples below show that scatterometry techniques in accordance with aspects of the invention have good sensitivity for measuring feature asymmetry, and can therefore be used for qualifying processes for which symmetric results might be desired, such as lithography and etch processing. Comparisons with other measurement technologies such as AFM and cross-section SEM show good consistency.

INDUSTRIAL APPLICABILITY

The invention is further illustrated by the following non-limiting examples.

To assess the viability of performing asymmetric profile measurements using scatterometry three different sample types were investigated (Examples 1-3). The first sample set was comprised of three wafers of photoresist lines on a metal substrate. The second sample was a single wafer of etched poly-Si. The third set was also a single wafer of grating lines printed in 193 nm photoresist. For each sample set the raw scatter signatures were obtained by performing measurements in a conical scanning orientation and through positive and negative angles. Suitable scatterometry libraries were generated for each sample set and included independent left and right variation in sidewall as well as the other parameters such as CD and thickness.

Example 4 illustrates the use of the invention to measure alignment of two successive layers on a semiconductor wafer.

EXAMPLE 1

Photoresist Lines on Metal Substrate

The line widths for this sample set were nominal 250 nm in width. The stack composition, from the top down, was comprised of the patterned photoresist on ARC on a TiN layer, followed by a thick AlCu layer (this effectively acted as the substrate).

Figure 6:
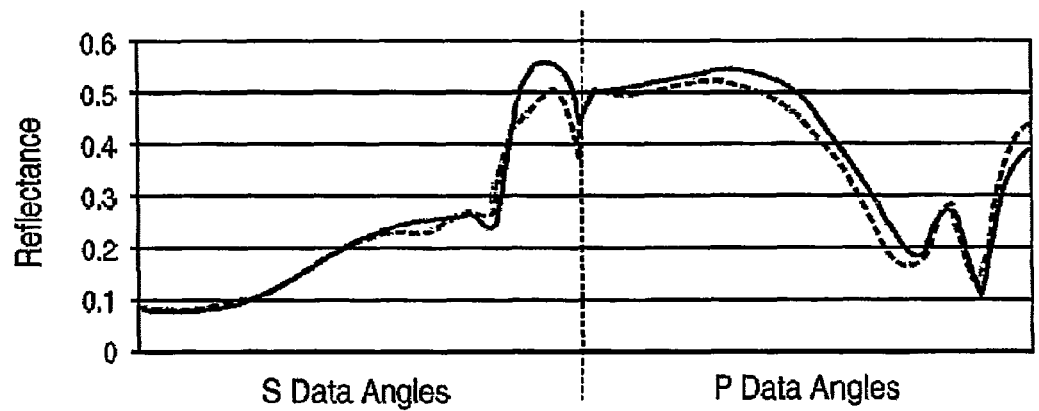
FIG. 6 is a graph of an angular scatterometry signature (mirrored) from metal resist wafers.

The raw signatures from this sample set showed a good deal of asymmetry. FIG. 6 depicts one signature from this data set with the positive and negative halves of the angular scan superimposed ("mirrored") on top of one another. Clearly, as the figure illustrates, the two halves are not the same. In fact, they differ at some angles by more than 5% in terms of reflectivity, and the structure of the signature differs at some angles as well. Because the measurements were made in the conical grating orientation, this is a sign of profile asymmetry.

Figure 7:
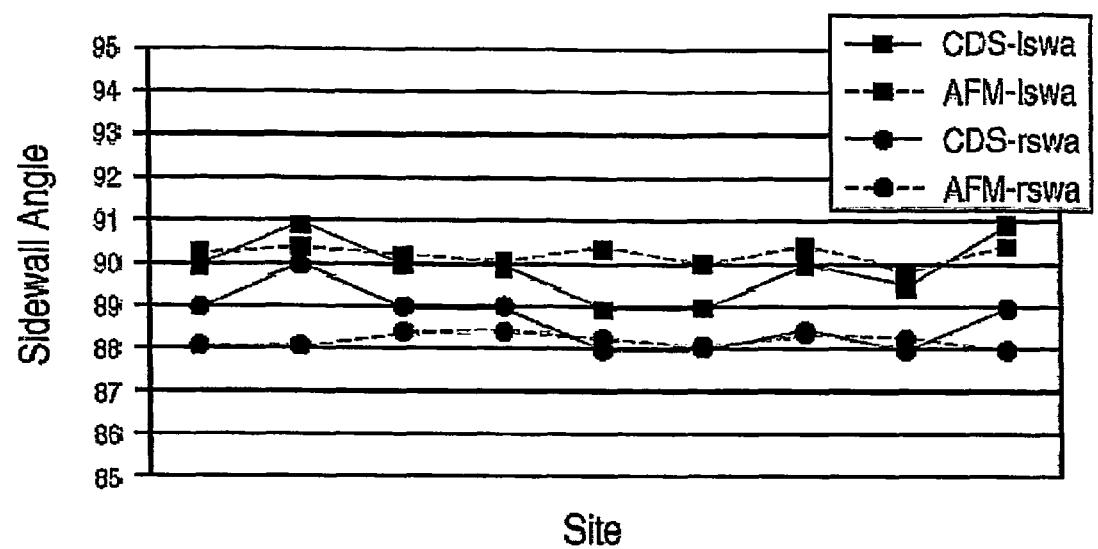
FIG. 7 is a graph of sidewall angle results from wafer 5 of the resist-on-metal sample set.

The raw signatures from this data set matched well to the model. Sidewall angle results from these wafer measurements can be seen in FIG. 7. Recall that the library allowed for independent variation in the left and right sidewall angles. In addition to the scatterometry measurements, AFM data from the same sites can be seen on this plot. Both the AFM and scatterometer results indicate that there is indeed a difference in the sidewall angles, and that it is in the range of 1-2 degrees. The data both agree that the left wall angle is steeper than the right wall angle as well. The scatterometry data indicate that the left and right angles move in tandem, i.e., that the overall width of the line does not change but rather "sways" by 1-2 degrees from site to site across the wafer. This effect could be due to correlation between the left and right wall angle parameters, but a check of the modeled signature data revealed that they are quite distinct when one wall angle is left fixed and the other allowed to vary.

EXAMPLE 2

Etched Poly-Si Lines

Figure 8:
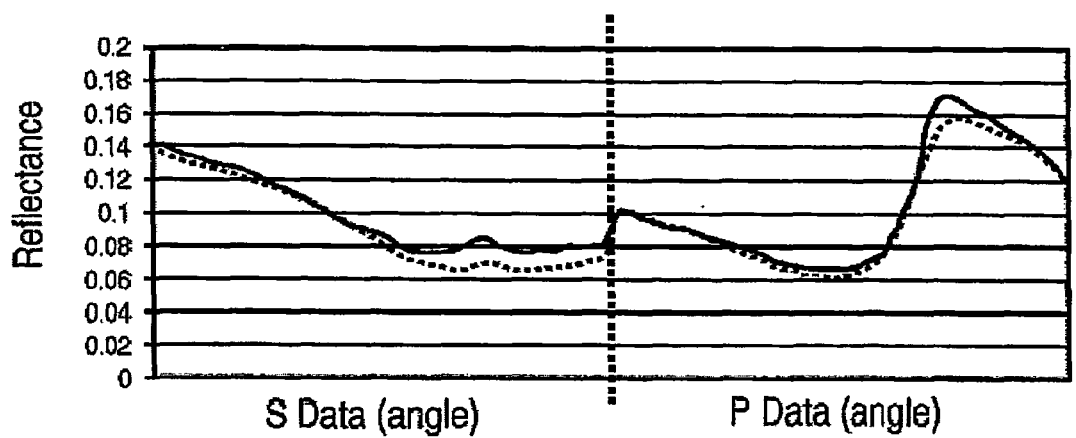
FIG. 8 is a graph of an angular scatterometry signature (mirrored) from an etched poly-silicon wafer.

The line widths for this sample set ranged from 150 to 300 nm. The stack was comprised of patterned (etched) poly-Si on oxide on Si substrate. The raw signatures from this sample set showed a slight amount of asymmetry when measured in the conical configuration. FIG. 8 depicts one such signature with both the positive and negative halves of the signature "mirrored" to illustrate this asymmetry.

Figure 9:
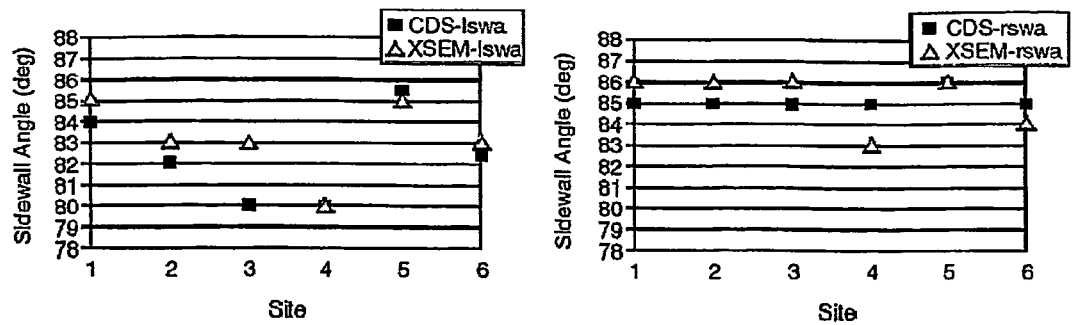
FIGS. 9(a) and (b) are, respectively, left and right sidewall angle comparisons between scatterometry and cross-section SEM for the etched poly-silicon wafer.

In order to draw comparisons, the wafer used for these scatterometry measurements was cross-sectioned and measured by a SEM to determine the sidewall angles of the lines. FIG. 9 shows the results of comparing the left and right sidewall angle measurements of the two technologies. As the figure illustrates, both tools are reporting some degree of sidewall asymmetry, with the left wall angle being generally smaller. Furthermore, the sidewall angle correlation between the two techniques is good and shows similar trending from site to site.

EXAMPLE 3

193 nm Photoresist Lines

The last sample set investigated was a single wafer of 193 nm photoresist lines printed on a BARC layer, a poly layer, an oxide layer and a silicon substrate. The nominal feature sizes on this wafer were 180 nm lines.

Figure 10:
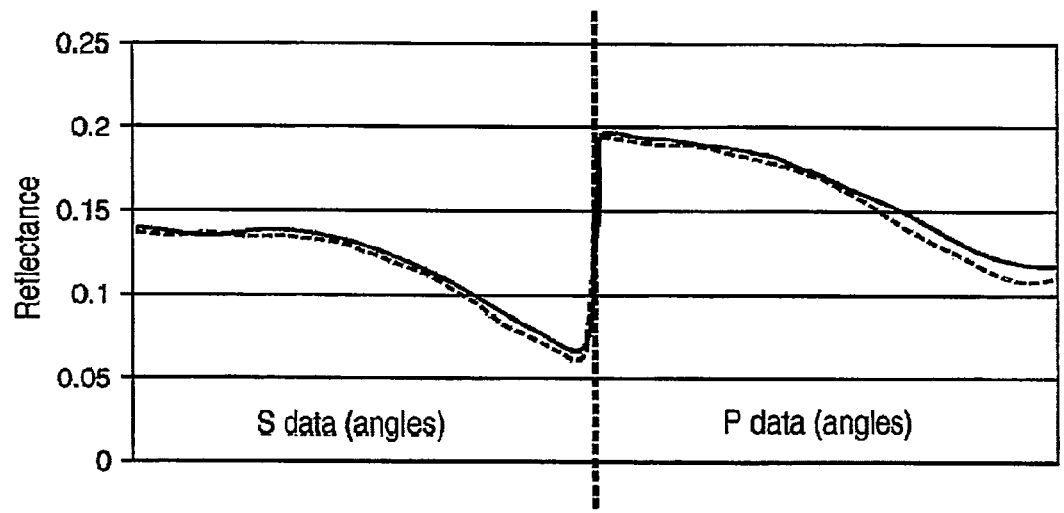
FIG. 10 is a graph of an angular scatterometry signature (mirrored) from a 193 nm resist wafer.

For this wafer, the signature data was only mildly asymmetric when measured in conical mode. FIG. 10 depicts the S and P polarizations for one of these signatures "mirrored" back upon itself. In contrast to the signature asymmetries observed from the previous samples, this asymmetry was relatively weak.

Figure 11:
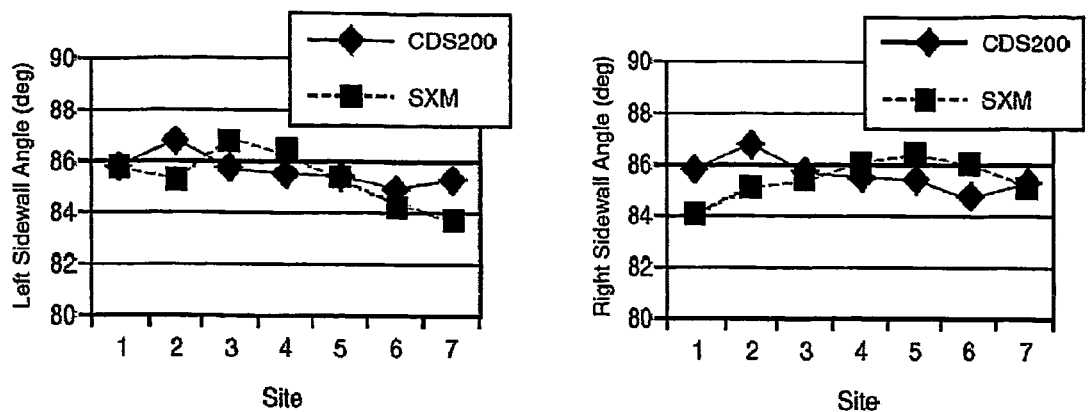
FIGS. 11(a) and (b) are, respectively, left and right sidewall angle comparisons between scatterometry and cross-section SEM for the 193 nm resist wafer.
Figure 12:
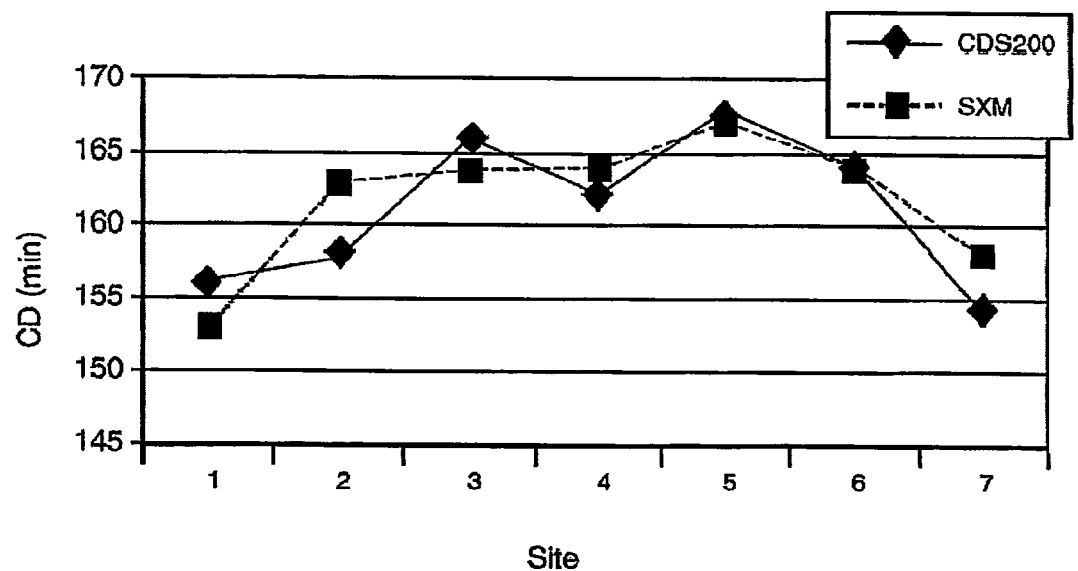
FIG. 12 is a comparison of AFM and scatterometry CD measurements for the 193 nm resist wafer.

The left and right wall angle data for one row from this wafer can be seen in FIG. 11. Included on the plots in this figure are measurements made on the same sites with an AFM. Both measurement technologies agree well in terms of the overall magnitude of the wall angles. The AFM data shows more asymmetric measurements but are generally consistent with the data from the scatterometer. A comparison of the CD measurements obtained by the scatterometer and AFM from this same row can be seen in FIG. 12. As this figure shows, the agreement between the AFM and scatterometer measurements is excellent. The average difference between these two techniques is 2.43 nm.

EXAMPLE 4

Successive Layer Alignment Measurement

The alignment of two successive layers on a semiconductor wafer is critical for the ultimate performance of the devices being manufactured. This alignment (also called overlay) is so important that there are tools dedicated to performing this one task. These tools are based on measuring images of special alignment marks printed at each layer. As the semiconductor industry moves towards smaller and smaller dimensions, however, there is a great deal of doubt surrounding the ability of these tools to provide the necessary measurement resolution.

Scatterometry is a technology well-suited for overlay measurements. By using a grating-on-grating structure, scatterometry measurements of the $0^{th}$, or specular, diffraction order are sensitive to alignment shifts in the successive grating layers. This shift in the grating layer (also referred to as an offset) results in an asymmetric line profile, and that can be measured using a scatterometer in the proper measurement orientation, and preferably (though not necessarily) with the ability to measure complementary angles (both positive and negative angles).

Figure 13:
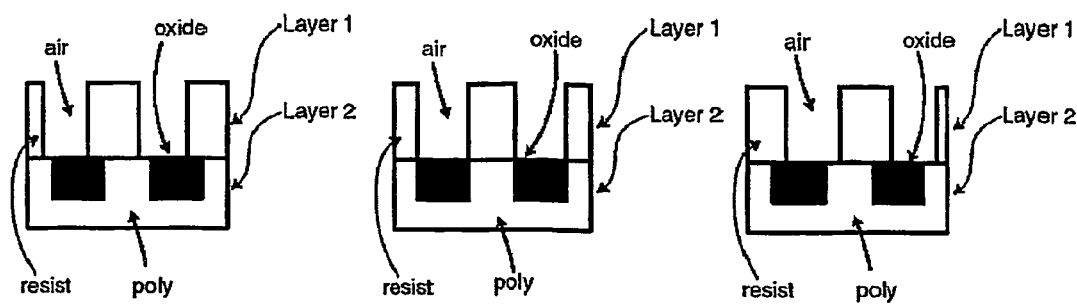
FIG. 13 shows images of a grating-on-grating profile that can be used for measurement of overlay misalignment.
Figure 14:
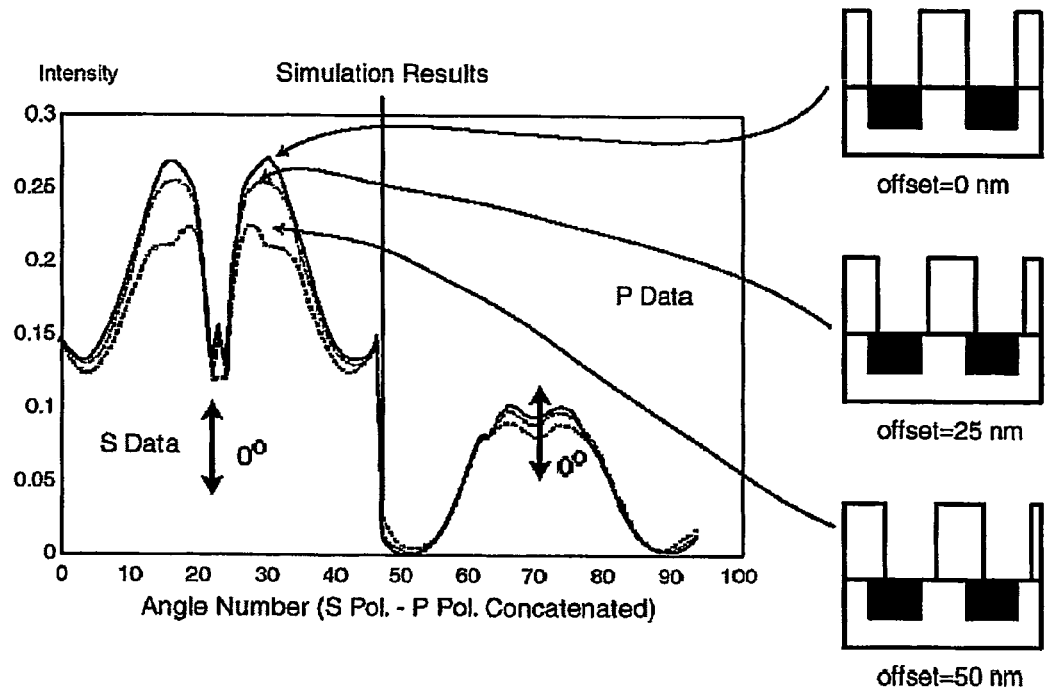
FIG. 14 is a graph of angular scatterometry signatures for the profiles of FIG. 13 employing a conventional (non-conical) scan.
Figure 15:
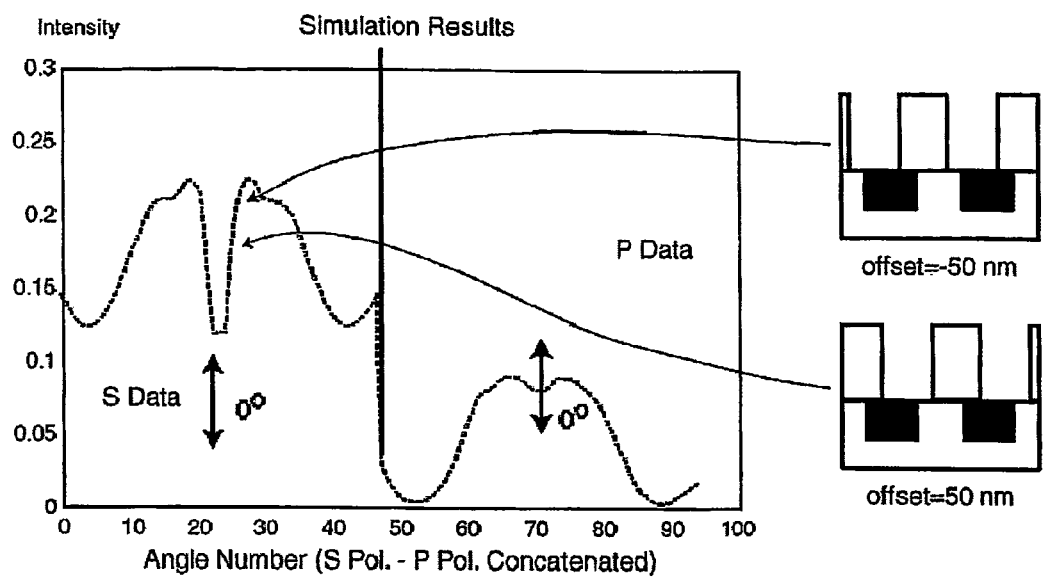
FIG. 15 is a graph of (non-unique) angular scatterometry signatures for left and right offsets employing a conventional scan.

FIG. 13 present images of a grating-on-grating profile that can be used for the measurement of overlay. Errors in aligning the two successive layers results in a shift between the grating lines, and an asymmetric line profile. FIG. 14 present results that demonstrate sensitivity to offsets or overlay errors for measurements performed in the conventional orientation (see FIG. 3(a)). The signatures change when offsets are introduced, which is a positive sign for general measurement sensitivity. However, as shown in FIG. 15, for a conventional scan the signatures that result when same magnitude +/− offsets are introduced are not unique. Hence, a conventional scan is less desirable than a conical scan.

Figure 16:
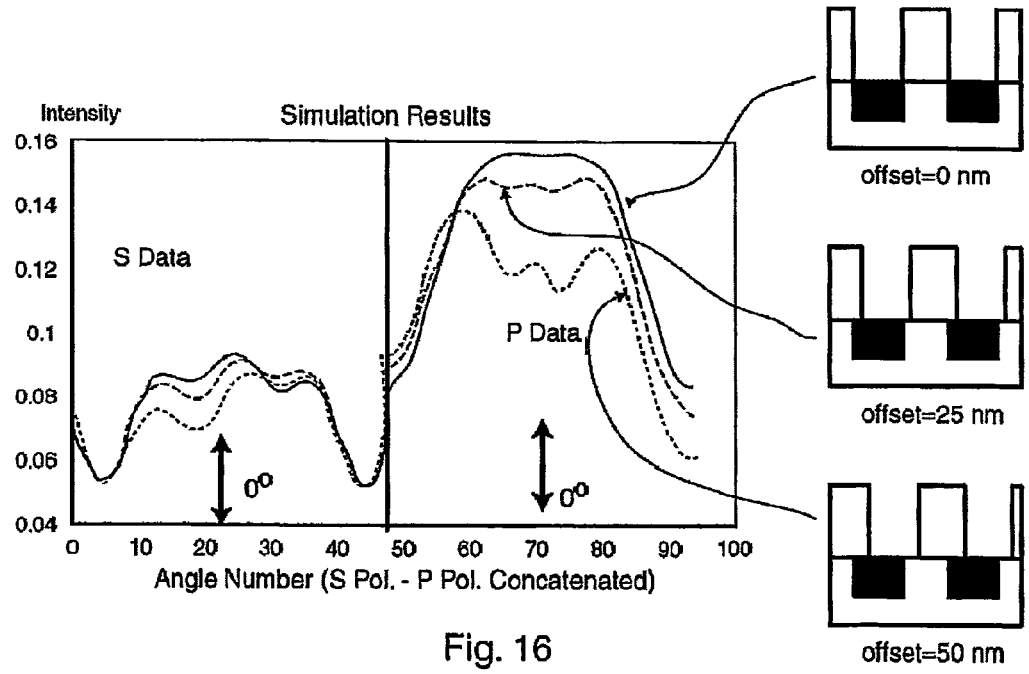
FIG. 16 is a graph of angular scatterometry signatures for the profiles of FIG. 14 employing a conical scan.
Figure 17:
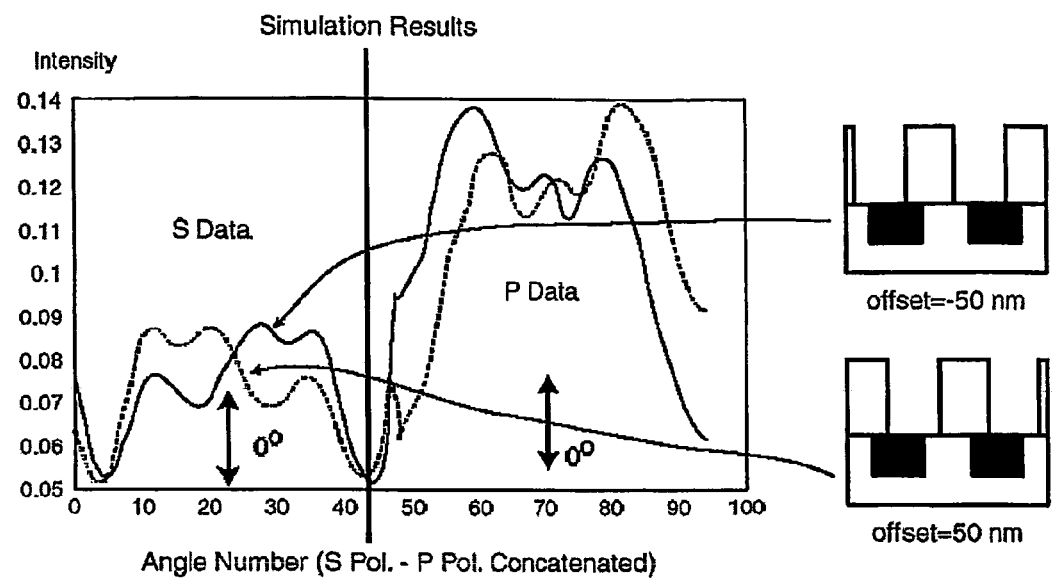
FIG. 17 is a graph of (unique) angular scatterometry signatures for left and right offsets employing a conical scan.
Figure 18:
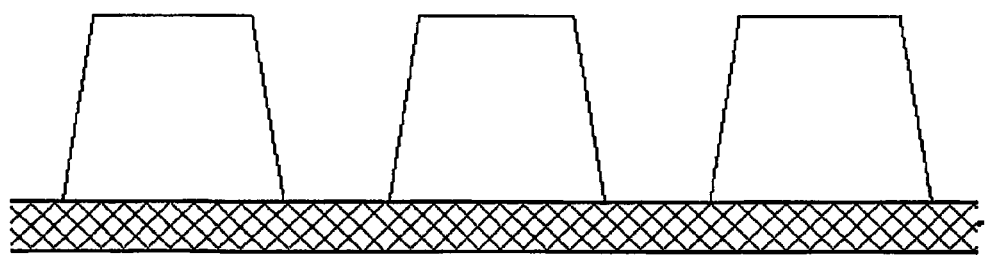
FIG. 18 illustrates an asymmetric single line model employed in the prior art, wherein the acute angles are equal to each other and the obtuse angles are equal to each other, such that the cross section of each line provides only two different angles.

Repeating the exercise with conical scans results in the signatures shown in FIGS. 16 and 17. As with conventional scans, FIG. 16 shows signature changes with offset, but FIG. 17 shows that changes are now unique as between +/− (left/right) offsets. Also note the symmetry about zero degrees.

Accordingly, investigation has shown that conventional and conical scans of the specular ($0^{th}$) order are both sensitive to offsets, but only conical scans provide unique signatures with respect to left/right shifts. Existing scatterometry methods for assessing overlays involve use of $1^{st}$ and higher orders and so require special measurement hardware to measure higher orders. See, e.g., Sohail Naqvi, et al., "Diffractive techniques for lithographic process monitoring and control", JVSTB 12(6) (November 1994) (moire interferometric technique using higher orders); and J. Bischoff, et al., "Light diffraction based overlay measurement", Proc. SPIE Vol. 4344, pp. 222-233 (2001) ($1^{st}$ order measurement of grating-in-grating).

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and the appended claims are intended to cover all such modifications and equivalents. The entire disclosures of all references, applications, patents, and publications cited above are hereby incorporated by reference.

What is claimed is:

1. A method of measuring three-dimensional structure asymmetries in microelectronic devices, the method comprising the steps of:
    directing light at an array of microelectronic features of a microelectronic device at least at a first angle of reflection and at least at a second angle of reflection, the first angle of reflection and the second angle of reflection being complementary angles of reflection, the light illuminating a portion of the array that encompasses the entire length and width of a plurality of the microelectronic features;
    detecting light scattered back from the array at a condition selected from the group consisting of one or more angles of reflection, one or more wavelengths, or a combination thereof for the complementary angles of reflection; and
    examining one or more characteristics of the back-scattered light by performing an operation comprising examining data from the complementary angles of reflection.

2. The method of claim 1 wherein the directing step comprises directing light at substantially a single wavelength.

3. The method of claim 1 wherein the directing step comprises directing light at a plurality of wavelengths.

4. The method of claim 1 wherein the examining step comprises comparing light intensity.

5. The method of claim 1 wherein the examining step additionally comprises comparing phase.

6. The method of claim 1 wherein the examining step additionally comprises comparing ratios of light magnitude and light phase.

7. The method of claim 1, wherein the directing step comprises directing light at the array of microelectronic features in general conical configuration.

8. The method of claim 1, wherein the directing and detecting steps are performed by an angular scatterometer.

9. The method of claim 1, wherein the directing and detecting steps are performed by a spectral scatterometer.

10. The method of claim 1, wherein the examining step comprises decomposing back-scattered light into S and P components relative to a plane of incidence.

11. The method of claim 1, wherein the detecting step comprises detecting specular order diffracted light.

12. The method of claim 1, additionally comprising the step of employing the results of the examining step to detect asymmetries selected from the group consisting of asymmetries within a single layer of the microelectronic device and asymmetries within multiple layers of the microelectronic device.

13. The method of claim 12 additionally comprising the step of controlling a manufacturing process if results of the comparing step indicate an asymmetry in the array.

14. A method of measuring line profile asymmetries in microelectronic devices, the method comprising the steps of:
   directing light at an array of microelectronic features of a microelectronic device at a first angle of incidence to the array and at a second angle of incidence to the array, the first angle of incidence and the second angle of incidence being complementary angles of incidence; detecting light scattered back from the array at angles complementary to the angle of incidence; and
   comparing one or more characteristics of the detected light to an asymmetric model that includes a single feature profile that, in transverse cross-section has an upper surface, a base and a midline extending between the upper surface and the base and perpendicularly to the base, wherein the cross section is asymmetrical about the midline.

15. The method of claim 14, wherein the transverse cross-section of the single feature profile includes at least three different internal angles.

16. The method of claim 14, wherein the transverse cross-section of the single feature profile includes four different internal angles.

17. The method of claim 14, wherein the single feature profile is of a first line and the model includes a feature profile of a second line overlaid on the first line, wherein at least one of the first line and the second line comprises at least three different internal angles on a transverse cross-section of the line.

18. The method of claim 17, wherein at least one of the first line and the second line has four different internal angles on a transverse cross-section of the line.

19. The method of claim 17, wherein both first line and the second line comprises at least three different internal angles on a transverse cross-section of each of the first line and the second line.

20. The method of claim 17, where the first line has at least one side wall that is offset from a second side wall of the second line.

21. The method of claim 20, wherein the first line has a first side wall that is aligned with a first side wall of the second line and a second side wall that is offset from a second side wall of the second wall.

22. The method of claim 14 wherein the directing step comprises directing light at substantially a single wavelength.

23. The method of claim 14 wherein the directing step comprises directing light at a plurality of wavelengths.

24. The method of claim 14 wherein the comparing step comprises comparing light intensity.

25. The method of claim 14 wherein the comparing step additionally comprises comparing phase.

26. The method of claim 14 wherein the comparing step additionally comprises comparing ratios of light magnitude and light phase.

27. The method of claim 14 wherein the directing step comprises directing light at the array of microelectronic features in general conical configuration.

28. The method of claim 14 wherein the directing and detecting steps are performed by an angular scatterometer.

29. The method of claim 14 wherein the directing and detecting steps are performed by a spectral scatterometer.

30. The method of claim 14 wherein the comparing step comprises decomposing the back-scattered light into S and P components relative to a plane of incidence.

31. The method of claim 14 wherein the detecting step comprises detecting specular order diffracted light.

32. The method of claim 14 additionally comprising the step of employing the results of the comparing step to detect asymmetries selected from the group consisting of asymmetries within a single layer of the microelectronic device and asymmetries within multiple layers of the microelectronic device.

33. The method of claim 32 additionally comprising the step of controlling a manufacturing process if results of the comparing step indicate an asymmetry in the array.

* * * * *